United States Patent
Zeng et al.

(10) Patent No.: US 6,379,586 B1
(45) Date of Patent: Apr. 30, 2002

(54) HYDROCARBON PARTIAL OXIDATION PROCESS

(75) Inventors: Yongxian Zeng, North Plainfield; Ravi Jain, Bridgewater; Satish S. Tamhankar, Scotch Plains; Donald L. MacLean, Clinton; Narayanan Ramprasad, Bridgewater, all of NJ (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 09/175,175

(22) Filed: Oct. 20, 1998

(51) Int. Cl.[7] .......................... C07C 1/02; C01B 31/18; C01B 3/02
(52) U.S. Cl. ................. 252/373; 423/418.2; 423/648.1
(58) Field of Search ...................... 252/373; 423/418.2, 423/648.1

(56) References Cited

U.S. PATENT DOCUMENTS

| | | | |
|---|---|---|---|
| 5,112,590 A | * 5/1992 | Krishnamurthy et al. | ... 423/415 |
| 5,149,516 A | * 9/1992 | Han et al. | ... 423/415 |
| 5,538,706 A | * 7/1996 | Kapoor et al. | ... 423/418.2 |
| 5,571,492 A | 11/1996 | Yao et al. | ... 423/263 |
| 5,714,091 A | 2/1998 | Mazanec et al. | ... 252/373 |
| 5,755,840 A | 5/1998 | Beer | ... 48/127.3 |

FOREIGN PATENT DOCUMENTS

| | | |
|---|---|---|
| EP | 0 913 184 A1 | 5/1999 |
| JP | 5-4044 | 1/1993 |

OTHER PUBLICATIONS

Patent Abstracts of Japan, vol. 017, No. 266 (C–1062), May 25, 1993 & JP 05 005044 A (Toyoda Gosei Co Ltd), Jan. 14, 1993 *abstract*.

* cited by examiner

Primary Examiner—Steven P. Griffin
Assistant Examiner—Jonas N. Strickland
(74) Attorney, Agent, or Firm—Philip H. Von Neida; Salvatore P. Pace

(57) ABSTRACT

Partial oxidation of hydrocarbons to produce hydrogen and carbon monoxide is carried out by a cyclical process which includes passing air through a perovskite ceramic substance at elevated temperature, thereby adsorbing oxygen from the air, and subsequently contacting the hot oxygen-containing ceramic substance with a hydrocarbon. During the partial oxidation reaction phase of the process, the sorbed oxygen reacts with the hydrocarbon, thereby producing the desired gas products and regenerating the adsorbent for the next cycle of the process.

45 Claims, 1 Drawing Sheet

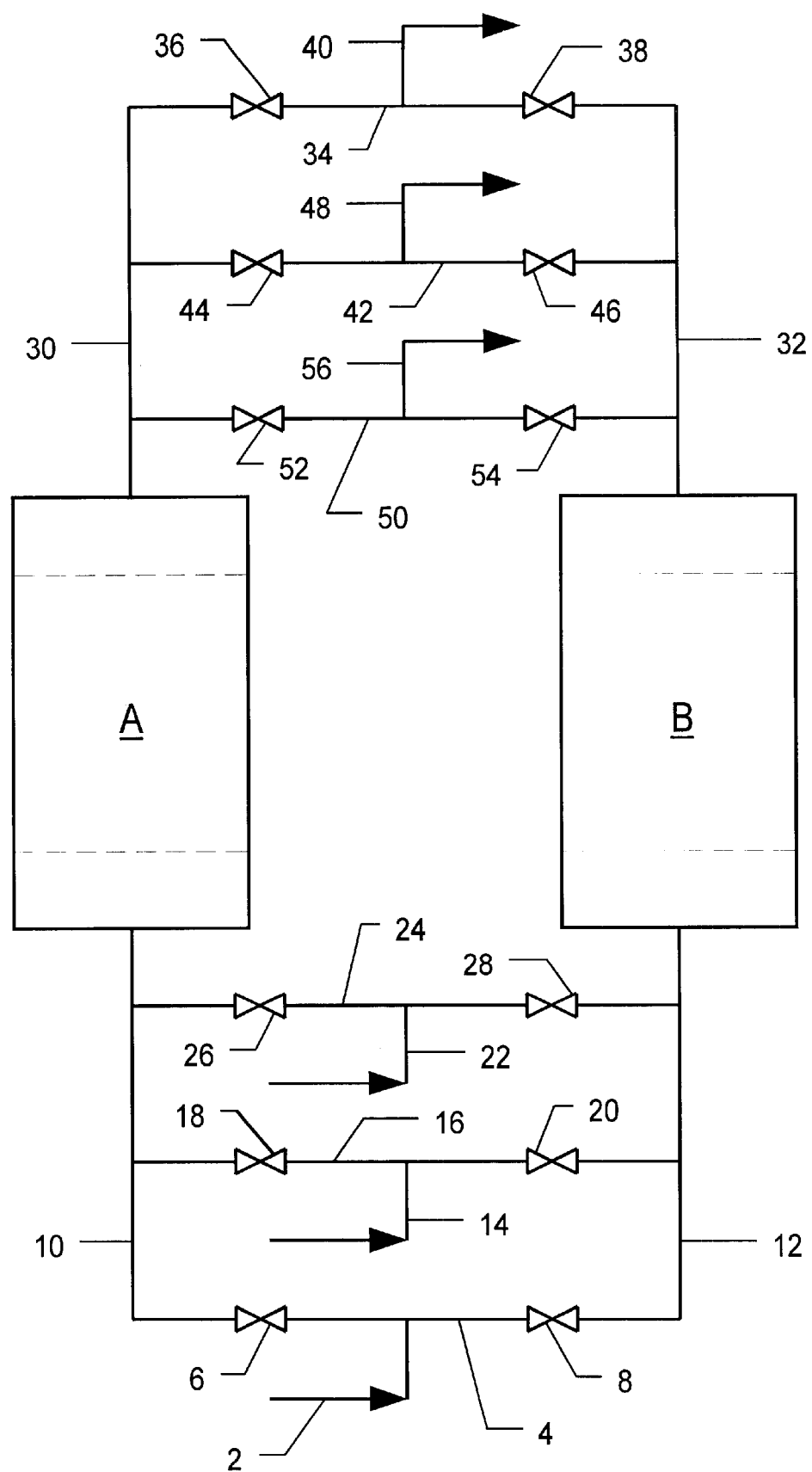

HYDROCARBON PARTIAL OXIDATION PROCESS

FIELD OF THE INVENTION

This invention relates to the partial oxidation of hydrocarbons, and more particularly to the production of hydrogen and carbon monoxide by the oxidation of hydrocarbons. Specifically, the invention relates to the high temperature adsorption of oxygen onto ceramic adsorbents and partial oxidation of hydrocarbons by contacting the hydrocarbons with the sorbed oxygen at elevated temperatures.

BACKGROUND OF THE INVENTION

Syngas and its components, hydrogen and carbon monoxide, are conventionally produced by the high temperature partial oxidation of hydrocarbons with controlled amounts of air or oxygen. Although air is less expensive and more convenient to use in partial oxidation reactions, it is less attractive than oxygen for such reactions because the large quantities of nitrogen that are produced when air is used as the oxidant must be subsequently separated from the product gas prior to its use. The cost of gas separation and purification equipment required to purify the product gas adds considerably to the cost of syngas production using air.

Although oxygen is more desirable than air as an oxidant for partial oxidation reactions, its use is not without disadvantage, in that oxygen must be imported into the system, or it must be generated on site, for example, by means of a cryogenic air separation plant or an adsorption system. In either alternative, using oxygen as the oxidant likewise adds considerably to the cost of the process.

More economical methods of on site production of oxygen for applications such as hydrocarbon partial oxidation reactions are continuously sought. U.S. Pat. No. 5,714,091 discloses an oxygen-based hydrocarbon partial oxidation process in which the oxygen is produced on site by subjecting air to membrane separation using a membrane constructed of perovskite-based ceramic material. Oxygen, which is permeable to the membrane, passes through the membrane and is made to react with hydrocarbons on the downstream side of the membrane unit. The disadvantages of this method of oxygen production are the high cost of production of the membrane and the difficulty of producing membrane structures that are leak-proof.

The present invention provides a system and process for the partial oxidation of hydrocarbons with oxygen that is produced from air in the partial oxidation reactor using a relatively inexpensive ceramic-based adsorbent material and a simple reactor design. The method of this invention has the additional advantage that the heat produced by the partial oxidation reaction can be used to increase the overall efficiency of the process by maintaining the adsorbent at the desired adsorption temperature without an external heat source.

SUMMARY OF THE INVENTION

According to a broad embodiment, the invention comprises a process for producing hydrogen and carbon monoxide by the partial oxidation of at least one hydrocarbon comprising the steps:

(a) passing an oxygen-containing gas at a temperature in the range of about 300 to about 1400° C. and at an absolute pressure in the range of about 0.5 to about 50 bara through at least one reaction zone containing an oxygen-selective mixed conductor, thereby preferentially adsorbing oxygen from said oxygen-containing gas; and (b) passing the at least one hydrocarbon through the at least one reaction zone at a temperature in the range of about 300 to about 1400° C., thereby producing a product gas comprising hydrogen, carbon monoxide or both hydrogen and carbon monoxide.

In a preferred embodiment of the invention, the oxygen-selective mixed conductor is selected from: (1) perovskite substances having the structural formula $A_{1-x}M_xBO_{3-\delta}$, where A is a rare earth ion, M is Sr, Ca, Ba or mixtures of these, B is Co, Mn, Cr, Fe or mixtures of these, x varies from 0 to 1 and $\delta$ is the deviation from stoichiometric composition resulting from the substitution of Sr, Ca and Ba for rare earth ions; (2) ceramic substances selected from $Bi_2O_3$, $ZrO_2$, $CeO_2$, $ThO_2$, $HfO_2$ and mixtures of these, the ceramic substance being doped with CaO, rare earth metal oxides or mixtures of these; (3) brownmillerite oxide; and (4) mixtures of any of these, In a more preferred embodiment of the invention, the oxygen-selective mixed conductor is a perovskite substance, and in a preferred aspect of this embodiment, x varies from about 0.1 to 1.

In another preferred embodiment, the oxygen-selective mixed conductor is a ceramic substance of group (2), above, and the ceramic substance is doped with a rare earth metal oxide selected from $Y_2O_3$, $Nb_2O_3$, $Sm_2O_3$, $Gd_2O_3$ and mixtures of these.

In another preferred embodiment, the oxygen-containing gas is air.

In another preferred embodiment, the process comprises repeatedly performing steps (a) and (b) in sequence in the above-mentioned at least one reaction zone.

In another preferred embodiment, the process further comprises, between steps (a) and (b), the additional step of removing nonadsorbed gas component from the adsorption vessel(s): (1) by purging the at least one reaction zone with gas that is compatible with the partial oxidation reaction product gas, (2) by depressurizing the at least one reaction zone or (3) by both purging the at least one reaction zone with gas that is compatible with the partial oxidation reaction product gas and depressurizing the at least one reaction zone. In a preferred aspect of this preferred embodiment, the gas that is used to purge the at least one reaction zone is oxygen, steam, carbon dioxide or mixtures of these.

In another preferred embodiment, the process further comprises, after step (b), removing residual product gas from the at least one adsorption zone: (1) by purging the at least one reaction zone with steam, carbon dioxide, nitrogen, argon, helium or mixtures of these, (2) by depressurizing the at least one reaction zone or (3) by both purging the at least one reaction zone with steam, carbon dioxide, nitrogen, argon, helium or mixtures of these and depressurizing the at least one reaction zone.

In another preferred embodiment, the at least one hydrocarbon has an aliphatic, cycloaliphatic or aromatic structure and it contains 1 to 12 carbon atoms.

In another preferred embodiment, the process is carried out at a temperature in the range of about 600 to about 1200° C.

In another preferred embodiment, step (a) of the process is carried out at an absolute pressure in the range of about 0.5 to 20 bara.

In a more preferred embodiment, the at least one hydrocarbon contains 1 to 6 carbon atoms.

In other preferred embodiments, the oxygen-selective mixed conductor is a perovskite substance and A is La, Y or mixtures of these and/or M is Sr, Ca or mixtures of these and/or B is Co, Fe or mixtures of these. More preferably, A is La, Y or mixtures of these, and/or M is Sr, Ca or mixtures of these and/or B is Co, Fe or mixtures of these.

In another preferred embodiment of the invention the oxygen-selective mixed conductor is a perovskite substance and x is 0.2 to 1.

In a most preferred embodiment, the process is carried out at a temperature in the range of about 750 to about 1100° C.

In a more preferred embodiment, the at least one hydrocarbon comprises 1 to 4 carbon atoms, and in one most preferred embodiment, it is methane. In another most preferred embodiment, the hydrocarbon feed gas is natural gas.

In another preferred embodiment, the at least one hydrocarbon comprises a petroleum derivative. In a more preferred embodiment, the petroleum derivative is naphtha, gasoline or mixtures thereof.

In another preferred embodiment, the at least one reaction zone contains particulate material having a thermal conductivity greater than that of the oxygen-selective mixed conductor. In one preferred aspect of this preferred embodiment, the high thermal conductivity particulate material is mixed with the oxygen-selective mixed conductor, and in another preferred aspect, the high thermal conductivity particulate is placed, upstream, downstream or both upstream and downstream of the oxygen-selective mixed conductor.

In another preferred embodiment, the at least one reaction zone additionally contains one or more catalysts for partial oxidation reactions. In a more preferred embodiment, the additional catalyst is deposited on the oxygen-selective mixed conductor.

In another preferred embodiment, the process of the invention further comprises, during step (b), passing a moderating agent selected from steam, carbon dioxide and mixtures of these through the at least one reaction zone. In a preferred aspect of this embodiment, the moderating agent is steam.

BRIEF DESCRIPTION OF THE DRAWINGS

FIG. 1 is a schematic representation of a two-reaction vessel system for practice of the process of the invention.

DETAILED DESCRIPTION OF THE INVENTION

The process of the invention is useful for carrying out partial oxidation processes that produce hydrogen and/or carbon monoxide and perhaps other products using as the oxidant substantially pure oxygen produced in the partial oxidation reaction chamber. The process of the invention is particularly useful for economically conducting partial oxidation processes in systems of any desired size. The oxygen adsorption step is carried out at high temperatures; accordingly, the adsorption step provides a high temperature environment for the partial oxidation process.

The oxygen is produced by adsorbing it from an oxygen-containing gas onto a ceramic substance which serves as the site of the partial oxidation reaction. By "oxygen-containing gas" is meant a gas that contains elemental oxygen. The Oxygen-containing gas may be substantially pure oxygen or oxygen-gas mixtures, such as oxygen-nitrogen mixtures, oxygen-argon mixtures, oxygen-nitrogen-argon mixtures, such as air, oxygen-carbon dioxide mixtures, oxygen-carbon monoxide mixtures, etc.

The preferred oxygen-containing gas is air, particularly ambient air, because of its low cost and ready availability.

The adsorption/partial oxidation process of the invention is preferably carried out on a cyclical basis. It comprises a high temperature oxygen adsorption step and a partial oxidation reaction step using the adsorbed oxygen as the oxidant. The process can be carried out in a system comprising a single adsorption/reaction unit or a battery of adsorption/reaction units operated in phase, or a plurality of adsorption/reactor units or batteries of adsorption/reaction units operated out of phase, whichever is desired. When a system comprising a single unit or a battery of units all of which are operated in phase is used, the adsorption and partial oxidation steps are necessarily intermittent, whereas when a plurality of units are employed in parallel and operated out of phase, one or more units can be in oxygen adsorption service while the partial oxidation reaction is being carried out in one or more other units. In preferred embodiments of the invention, adsorption/partial oxidation cycles are repeatedly carried out in a manner such that production of the desired partial oxidation products is substantially continuous.

The adsorbent/catalyst used in the process of this invention is an oxygen-selective mixed conductor. By "oxygen-selective mixed conductor" is meant a ceramic material that exhibits both oxygen ion conductivity and electronic conductivity. Properties of oxygen-selective mixed conductors are set forth in Lin et al., "Oxygen Permeation through Thin Mixed Conducting Solid Oxide Membranes", AIChE Journal, May 1994, Vol. 40, No. 5, pp. 786–798, the text of which is incorporated herein by reference.

Preferred oxygen-selective mixed conductors include ceramic materials selected from: (1) perovskite substances having the structural formula $A_{1-x}M_xBO_{3-\delta}$, where A is a rare earth ion, M is Sr, Ca, Ba or mixtures of these, B is Co, Mn, Cr, Fe or mixtures of these, x varies from >0 to 1 and $\delta$ is the deviation from stoichiometric composition resulting from the substitution of Sr, Ca and Ba for rare earth ions; (2) ceramic materials selected from compounds such as $Bi_2O_3$, $ZrO_2$, $CeO_2$, $ThO_2$, $HfO_2$ and mixtures of these, wherein the ceramic material is doped with CaO, a rare earth metal oxides, such as, for example, $Y_2O_3$, $Nb_2O_3$, $Sm_2O_3$, $Gd_2O_3$ and mixtures of these; a brownmillerite oxide; and mixtures of any of these.

In a preferred embodiment the ceramic oxygen-adsorbing material is a ceramic substance having the perovskite structure. When the ceramic material is a perovskite, the maximum oxygen adsorbing capability is attained when x, in the formula above, has a value of 1. Although oxygen adsorption can occur when the value of x in the perovskite compound used in the process is 0, it is generally not commercially feasible to use perovskite compounds having a value of x less than about 0.01 in the process of the invention. Preferably x has a value of about 0.1 to 1, and most preferably it has a value of about 0.2 to 1. Details of the adsorption step of the process are set forth in the copending U.S. patent application entitled High Temperature Adsorption Process, filed of even date herewith, the specification of which is incorporated herein by reference.

When the ceramic material is perovskite, the preferred rare earth ions for use in the process of the invention are La and Y, and the preferred divalent cations are Sr and Ca. Also, B is preferably Co or Fe. Typical of perovskite adsorbents suitable for use in the invention are $La_{1-x}Sr_xBO_{3-\delta}$, $Y_{1-x}Sr_xBO_{3-\delta}$ $Y_{1-x}Ca_xBO_{3-\delta}$, and combinations of these, wherein B is Co, Mn, Cr or Fe. Specific useful perovskite adsorbents are materials having the structural formulas: $La_{0.8}Sr_{0.2}MnO_{3-\delta}$, $La_{0.7}Ca_{0.3}FeO_{3-\delta}$, $Y_{0.9}Sr_{0.1}CrO_{3-\delta}$, $SrCoO_3$, etc. In the last compound, $SrCoO_3$, x has a value of 1.

The minimum temperature at which the adsorption step of the process of the invention is carried out is generally at least about 300° C. This step is preferably carried out at temperatures of at least about 600° C., and most preferably carried out at temperatures of at least about 750° C. The upper temperature limit for carrying out the adsorption step is below the temperature at which the oxygen-selective adsorbent begins to melt. Generally the maximum upper temperature is not in excess of about 1400° C. Preferably, the adsorption step is carried out at temperatures not exceeding about 1200° C., and this step is most preferably carried out at temperatures not in excess of about 1100° C. The partial oxidation step of the process is generally carried out at or near the temperature at which the adsorption step is carried out.

Since the partial oxidation step of the process is highly exothermic, the temperature in the reaction zone tends to rise as the reaction step of the cycle proceeds. It is often desirable to recover the significant quantity of heat generated during the process. This can be conveniently accomplished by including thermal ballast in the system. The ballast may be, for example, in the form of particles of materials having high thermal conductivities. The high thermal conductivity material may be mixed with the oxygen-selective-adsorbent, or it may comprise an independent layer upstream and/or downstream of the layer of the oxygen-selective adsorbent material. In the latter alternative it is often desirable to position the layer of high thermal conductivity material on the downstream side of the oxygen-selective-adsorbent with respect to the direction of flow of gas through the reaction vessel during the partial oxidation step of the process. The reason for this is that heat can be captured from the hot gases leaving the reaction zone after the partial oxidation reaction. This serves the dual purpose of cooling the product gas stream and storing heat for use in heating air being fed into the reaction zone during the following adsorption step of the process. To this end it may be preferable to operate the system in a manner such that fresh air feed and hot product gas flow through the reaction vessel in opposite directions relative to each other. When this counterflow arrangement is employed it may be preferable to position the layer of high thermal conductivity material at the air inlet end (hot reaction gas outlet end) of the reaction vessel so that the hot gases exiting the reaction zone heat the high conductivity material just prior to the passage of feed air through the high thermal conductivity material during the next succeeding adsorption step of the process.

The pressure at which the adsorption step of the process is carried out is a matter of choice and not critical. In general, this step is usually carried out at a pressure at or above about 1 bar, absolute (bara). High pressures are generally preferred over low pressures because the adsorbent has a greater capacity for oxygen at high pressures. The minimum pressure at which the adsorption step is carried out is preferably about 0.5 bara and is most preferably about 5 bara. The upper pressure limit of the adsorption step of the process is determined by economics and limitations of the reaction system and, in general, this step is desirably carried out at absolute pressures not in excess of about 50 bara, is preferably carried out at pressures not in excess of about 20 bara, and is most preferably carried out at pressures not in excess of about 15 bara.

The pressure at which the partial oxidation step is carried out is likewise a matter of choice and not critical. It is convenient to carry out the partial oxidation step at or below the pressure at which the adsorption step is carried out.

It may be desirable to include a purge or evacuation step between the adsorption step and the partial oxidation step to remove from the reaction vessel any residual gas components that it is not desired to include in the partial oxidation step product stream. For instance, when the oxidant feed to the system is air, it may be desirable to discharge residual nitrogen from the reaction chamber to avoid diluting the partial oxidation reaction gas product stream with nitrogen. This can be accomplished, for example, by purging the reaction chamber with a gaseous substance that is compatible with the partial oxidation product gas. By "compatible" is meant that the purge gas will be consumed during the partial oxidation reaction, or that it is easily separable from the product gas or that the presence of the purge gas in the reaction product gas is not objectionable with respect to the intended use or further processing of the product gas. Suitable purge gases include substantially pure oxygen, steam and carbon dioxide. When oxygen is used as the purge gas, it may be obtained from, for example, another adsorption/reaction vessel of the system that is undergoing its adsorption step, or from storage.

As an alternative to purging, or in addition to purging, the reaction chamber can be evacuated upon completion of the adsorption step of the process. If the reaction chamber is evacuated between the oxygen adsorption step and the partial oxidation reaction step, it is preferred to avoid conducting the evacuation step to the extent that significant quantities of sorbed oxygen are desorbed from the adsorbent, since this reduces the overall efficiency of the process. When evacuation is carried out at this stage of the process, the pressure in the reaction chamber is preferably not reduced to below about 0.5 bara, and is most preferably not reduced to pressures below about 1 bara. Any suitable gas pumping means, such as a vacuum pump can be used for this step of the process.

It may also be desirable to include an evacuation step and/or a purge step after the partial oxidation step of the process but before the adsorption step of the next succeeding cycle to recover or remove any product gas remaining in the reaction chamber after the partial oxidation step. This can be accomplished by evacuating the reaction chamber with the same or different gas pumping means that is used for the post adsorption step evacuation step. This evacuation step can be carried out to any desired pressure. For example, the pressure can be reduced to about 0.1 bara or lower, but, for economic purposes, it is preferably not reduced to below about 0.2 bara at this stage of the process. Alternatively to, or in addition to, evacuation, residual product gas remaining in the reaction vessel upon completion of the partial oxidation reaction step can be at least partially removed from the vessel by purging the reaction vessel with a suitable gaseous substance, such as carbon dioxide or steam.

In a variation of the partial oxidation reaction described above, water, preferably in the form of steam, carbon dioxide or both of these can be passed through the reaction zone with the hydrocarbon. In this variation, steam- or carbon dioxide-reforming of the hydrocarbon occurs in addition to partial oxidation of the hydrocarbon. The steam and/or carbon dioxide reforming reaction can take place even after substantially all of the sorbed oxygen is consumed by the partial oxidation reaction. Since the partial oxidation reaction is highly exothermic and the reforming reaction is endothermic, the reforming reaction may also serve the useful function of moderating the temperature in the reaction zone. On the other hand, it may be desirable or necessary in some cases to provide supplemental heat to the reaction zone to compensate for heat consumed in the reforming reaction. Supplemental heat can be provided by any suitable means, such as by the use of heaters.

If desired, the partial oxidation step of the process can be used to produce partial oxidation products other than carbon monoxide and hydrogen. This can be accomplished by including in the reaction chamber a catalyst which promotes the desired partial oxidation reaction and using the appropriate hydrocarbon as the feed stream. Typical of such partial oxidation product manufacturing processes are:

1. The manufacture of cyclic anhydrides by the reaction of aromatic compounds or straight-chained $C_4$ hydrocarbons with oxygen in the presence of a vanadium-based catalyst. Examples include the production of maleic anhydride by the reaction of benzene or a saturated or unsaturated $C_4$ hydrocarbon such as butane or butene with oxygen and the manufacture of phthalic anhydride by the reaction of p-xylene or naphthalene with oxygen.

2. The manufacture of alkylene oxides by the reaction of lower alkanes or alkenes with oxygen in the presence of a silver oxide catalyst supported on silica or alumina or mixed molten nitrate salts. An example is the reaction of propane or propylene with oxygen in the presence of molten sodium and potassium nitrates to produce propylene oxide.

3. The manufacture of chlorinated hydrocarbons by the reaction of lower alkanes or alkenes with oxygen and hydrogen chloride or chlorine in the presence of a copper chloride catalyst supported on silica or alumina. Examples include the reaction of ethylene or ethane with oxygen and hydrogen chloride or chlorine to produce vinyl chloride or ethylene dichloride.

4. The manufacture of aldehydes by the reaction of lower alkanes or alkenes with oxygen in the presence of various metal halides or metal oxide catalysts. Examples include the production of acetaldehyde by the reaction of ethylene with oxygen in the presence of copper chloride and palladium chloride, and the manufacture of acrolein by the reaction of propane or propylene with oxygen over a molybdenum-bismuth-iron catalyst.

5. The manufacture of olefinically unsaturated nitriles by the reaction of lower alkanes or alkenes with oxygen and ammonia in the presence of a bismuth molybdenum oxide catalyst or an iron antimony oxide catalyst supported on silica or alumina. Examples of this type of process include the production of acrylonitrile by the reaction of propane or propylene with oxygen and ammonia and the production of methacrylonitrile by the reaction of i-butane or i-butylene with oxygen and ammonia.

The oxygen-containing gas may be air, oxygen-enriched air, or other oxygen-inert gas mixtures. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. The most preferred oxidant for use in the invention is air.

The particular hydrocarbon or hydrocarbons used as reactant in the hydrocarbon partial oxidation step of the process of the invention is a matter of choice. When the partial oxidation process is used to simply produce hydrogen and carbon monoxide, the hydrocarbon used as feed may be any aliphatic, cycloaliphatic or aromatic hydrocarbon having 1 to 12 or more carbon atoms, and it may be saturated or ethylenically unsaturated and straight chain or branched chain. Preferred hydrocarbons are the aliphatic hydrocarbons having 1 to 6 carbon atoms, and more preferred hydrocarbon feeds are comprised of one or more hydrocarbons having 1 to 4 carbon atoms. Typical of suitable hydrocarbon feed substances are methane, ethane, propane, the butanes, benzene, the xylenes, refined petroleum fractions, such as naphtha and gasoline, etc. Preferred hydrocarbon feeds include methane, ethane, ethene, propane, propene and the $C_4$ hydrocarbons. Most preferred hydrocarbon feeds for the production of hydrogen and carbon monoxide by the process of the invention are methane and natural gas.

When the partial oxidation process is used to produce compounds other than hydrogen and carbon monoxide, the feed hydrocarbon may be one or more aromatic, aliphatic or cycloaliphatic compounds, and it may be saturated or ethylenically unsaturated and straight chain or branched. Suitable aromatic hydrocarbons include those having up to twelve or more carbon atoms and suitable aliphatic and cycloaliphatic hydrocarbons include those having two to twelve or more carbon atoms. Preferred aromatic hydrocarbons are those having six to ten carbon atoms, such as benzene, the xylenes and naphthalene, and preferred aliphatic hydrocarbons are the saturated or ethylenically unsaturated straight-chain hydrocarbons having two to six hydrocarbon atoms, such as ethane, ethene, propane, propylene, n-butane, i-butane, n-butylene, i-butylene, butadiene, and the pentanes, pentenes, hexanes and hexenes.

The invention can be more easily understood by reference to the appended drawing, considered in conjunction with the following description. Equipment that is not necessary for an understanding of the invention, such as auxiliary valves, pumps, storage vessels and pumps, have not been included in the illustrated system.

Turning now to the drawing, illustrated therein is a two vessel partial oxidation system containing a pair of reaction vessels, A and B, arranged in parallel. Vessels A and B are packed with a particulate adsorbent of the type described above, for example a perovskite ceramic material of the type described above. At the inlet end, the system is provided with air feed line 2, which is connected to manifold 4. Manifold 4 can be put into fluid communication with reaction vessel feed lines 10 and 12 via valves 6 and 8, respectively. Lines 10 and 12 are connected to the inlet end of reaction vessels A and B, respectively. The inlet end of the system is also provided with hydrocarbon feed line 14, which is attached to manifold 16 at a point between valves 18 and 20, also provided in manifold 16. Manifold 16 can be put into fluid communication with lines 10 and 12 via valves 18 and 20, respectively. Purge gas inlet line 22 is connected to manifold 24, which, in turn, communicates with lines 10 and 12 via valves 26 and 28, which are located in manifold 24.

On their outlet ends, vessels A and B are connected to lines 30 and 32, respectively. Lines 30 and 32 are connected to manifold 34, and flow to manifold 34 from lines 30 and 32 is provided by valves 36 and 38, which are attached to manifold 34. Also attached to manifold 34, at a point between valves 36 and 38, is nitrogen gas discharge line 40. Lines 30 and 32 can be put into fluid communication with manifold 42 through valves 44 and 46, respectively, which are positioned in manifold 48. Manifold 48 is connected to partial oxidation reaction product gas line 48 at a point between valves 44 and 46. Additionally attached to lines 30 and 32 is manifold 50. Flow to manifold 50 from lines 30 and 32 is provided by valves 52 and 54, respectively, which are positioned in manifold 50. Purge gas discharge line 56 is connected to manifold 50 at a point between valves 52 and 54.

The system illustrated in the drawing is designed to be operated in semi-continuous fashion, with reactors A and B being operated 180° out of phase, so that reactor A is in oxygen adsorption service while reactor B is in partial oxidation reaction service, and vice versa. The process of the invention, as carried out in the system illustrated in the drawing, will be described as a two-stage process comprising a first stage, in which reactor A is in oxygen adsorption mode and reactor B is in partial oxidation reaction mode, and a second stage, in which reactor B is in adsorption mode and reactor A is in partial oxidation mode.

At the beginning of the first stage, valves 6, 20, 36 and 46 are open and all other valves are closed. Air, introduced into the system through line 2, passes through line 10 and enters vessel A. The air may be blown into the system by means of a compressor, a blower, or other gas pumping means positioned in line 2. An air drying step is not ordinarily necessary or desirable in the process of the invention, since only oxygen will be adsorbed by the oxygen-selective adsorbent. Moisture and other impurities, such as carbon dioxide, will be discharged from the system with the nonadsorbed waste gas stream.

During the adsorption stage of the process the adsorbent in vessel A is maintained at a temperature in the range of about 600 to about 1400° C. Initial heating of the adsorbent can be accomplished by heating the feed air before it enters vessel A or by heating the adsorbent in vessel A. Heating of the feed air or adsorbent can be accomplished by any suitable means, such as by means of external heating devices. When it is desired to heat the adsorbent in addition to or instead of heating the incoming air, this can be accomplished by suitable method, such as by use of electric heating means, by incorporating the reaction zone in a furnace zone or by combusting fuel and passing the hot combustion gases through the reaction zone prior to introduction of air thereinto. The method used to heat the adsorbent in reaction vessels A and B is a matter of choice and forms no part of this invention.

Once the adsorbent in vessels A and B reaches the desired reaction temperature, it is generally not necessary to continue applying heat to the reaction zone to maintain the adsorbent at the desired adsorption and partial oxidation reaction temperature since the heat of adsorption during the oxygen adsorption step and the heat of combustion during the partial oxidation step is adequate to accomplish this. Distribution of heat in the reaction zone can, if desired, be facilitated by incorporating a material having a high thermal conductivity into the reaction zone. As mentioned above, this can be accomplished mixing or sandwiching, i. e. layering, the oxygen-selective adsorbent with a high temperature stable material, such as a heat conducting ceramic material or a particulate metal material. Heat flow in the reaction zone can also be accomplished by inserting strips or rods of metallic material in, upstream or downstream of the reaction zones. If it is desirable or necessary to remove heat from the reaction zone to prevent excessive heating of the adsorbent contained therein, this can be accomplished by means of the above-described heat transmission means.

In any event, the air feedstream entering vessel A passes upwardly through the adsorbent contained therein, and as it does so oxygen is adsorbed by the adsorbent. Nonadsorbed gas, comprised substantially of nitrogen and argon when air is the feed, leaves vessel A through line 30 and passes out of the system through manifold 34 and line 40. The nitrogen may be collected as a byproduct gas stream, or it can be discharged to the atmosphere. As the adsorption step proceeds in vessel A, the adsorbed oxygen forms a front which advances through the bed of adsorbent toward the nonadsorbed product outlet end of vessel A.

While the oxygen adsorption step is taking place in vessel A the partial oxidation step is initiated and carried on in vessel B. During this stage of the cycle, a hydrocarbon gas, such as methane or natural gas, is introduced into vessel B through lines 14 and 12. If desired, the hydrocarbon feed may be compressed to the desired pressure by any suitable means, such as by a compressor or gas blower, or the gas may be provided from its source as a pressurized gas stream. As the hydrocarbon gas contacts the hot adsorbent in vessel B, it reacts with the oxygen sorbed onto the adsorbent to produce the desired partial oxidation gas product, which is generally a mixture of hydrogen and carbon monoxide. The product gas stream may also contain other gaseous by-products, such as carbon dioxide and moisture, but the concentration of these by-products can be minimized by maintaining optimum reaction conditions in the reaction vessel. The hot reaction gases pass out of vessel B through lines 32 and 48 and they pass, for example, to storage or downstream processing units. As the partial oxidation reaction progresses in vessel B, the adsorbent in this vessel is regenerated by removal of the sorbed oxygen therefrom.

At a predetermined point in the first stage of the process, such as when the adsorbed oxygen front reaches a desired point in vessel A, or when all of the oxygen in vessel B is reacted with hydrocarbon, the first stage of the cycle is terminated and the second stage begins. By proper sizing of the reaction vessels and careful control of the reactant gas flow rates, etc., the process can be designed so that the adsorption step in vessel A reaches its desired end point at substantially the same time that all of the sorbed oxygen in vessel B is reacted. Alternatively, if the adsorption step in vessel A reaches its desired end point before the oxygen in vessel B is completely reacted, or vice versa, the completed part of the first stage of the process can be terminated and further activity in that vessel can be suspended until the other part of the first stage reaches its desired end point.

Upon completion of the first stage of the process, the second stage is begun. During the second stage valves 8, 18, 38 and 44 are open and all other valves are closed. Air, introduced into the system through line 2, now passes through line 12 and enters vessel B. As the air passes through vessel B, oxygen is adsorbed by the regenerated perovskite adsorbent in this vessel. Nonadsorbed gas now passes out of vessel B through line 32 and leaves the system through line 40. Meanwhile, the partial oxidation step is initiated and carried on in vessel A. During this stage of the cycle, hydrocarbon gas is introduced into vessel A through lines 14 and 10. As the hydrocarbon gas contacts the hot adsorbent in vessel A, it reacts with the oxygen sorbed onto the perovskite adsorbent to produce the desired partial oxidation gas product. The hot reaction gases pass out of vessel A through line 30 and passes out of the system through line 48.

When the desired stage 2 end point is reached, the second stage of the process (and the current cycle) ends and the next cycle begins with vessel A in oxygen adsorption mode and vessel B in partial oxidation reaction mode.

To increase the overall efficiency of the process of the invention, it may be desirable to include a step for removing residual nonadsorbed gas component from the vessel undergoing oxygen following completion of this step. This can be accomplished in the manner described above, by purging the vessel completing its adsorption step with a gas that is compatible with the partial oxidation reaction product gas, such as oxygen, steam or carbon dioxide, or by evacuating the vessel to desired extent without significantly desorbing oxygen from the adsorbent. It can be appreciated that evacuating the vessel and/or purging the vessel with steam and/or carbon dioxide is usually preferable to purging the vessel with oxygen, since these methods avoid the necessity of supplying pure oxygen to the system.

In any event, if it is desired to purge the reaction vessel completing its adsorption step, this can be accomplished by closing the relevant valves in manifolds 4 and 34 and opening the relevant valves in manifolds 24 and 50. For example, when it is desired to purge vessel A upon completion of its oxygen adsorption step, purging of vessel A can be accomplished by closing valves 6 and 36 and opening valves 26 and 44; and when it is desired to purge vessel B upon completion of its oxygen adsorption step, purging of vessel B can be accomplished by closing valves 8 and 38 and opening valves 28 and 46. The duration of the cycle can be adjusted as necessary or desired to balance operation of the steps taking place in each reaction vessel.

When it is desired to evacuate the vessel completing its adsorption step, this can be accomplished by providing a gas pumping means, such as a vacuum pump, in line 40 to remove residual nonadsorbed gas from that vessel. As indicated above, this is the desired alternative. As an alterative, both oxygen purging and vessel evacuation can be carried out, if desired. When only evacuation of the vessel completing its oxygen adsorption step is to be carried out, manifolds 24 and 50 and the valves associated with these manifolds can be eliminated from the system.

It may also be desirable to conduct evacuation of the vessel completing its partial oxidation step of the process. This can be accomplished by providing a gas pumping means, such as a vacuum pump, in line 48. Evacuation of the vessel in which the partial oxidation step is taking place can be carried out during and/or upon completion of the partial oxidation step.

In a more preferred embodiment of the invention, both evacuation of the vessel undergoing or completing its adsorption step and evacuation of the vessel undergoing or completing its partial oxidation step are carried out. This can be conveniently carried out by evacuating both vessels simultaneously during or upon completion of the adsorption step and partial oxidation step taking place in the vessels. In this case, when a two vessel system is used for practice of the process, two gas pumping means are required.

It will be appreciated that it is within the scope of the present invention to utilize conventional equipment to monitor and automatically regulate the flow of gases within the system so that it can be fully automated to run continuously in an efficient manner.

The invention is further illustrated by the following example in which, unless otherwise indicated, parts, percentages and ratios are on a volume basis.

EXAMPLE

An alumina tube reactor 22 inches long and having an outside diameter of 0.25 was packed with 1.67 g of $La_{0.8}Sr_{0.2}Co_{0.5}Fe_{0.5}O_{3-\delta}$ perovskite particulate ceramic material having a particle size of about 50 microns. The reactor was heated to 900° C. by means of a tubular electric furnace. Air was then passed through the reactor at a flow rate of 50 ml/min(STP) for about 10 minutes. Oxygen adsorption was monitored during this step by recording oxygen breakthrough. Following this step, a gas stream containing 20% methane and 80% nitrogen was passed through the reactor for a period of 20 minutes at a flow rate of 50 ml(STP)/min while maintaining the temperature in the reactor at about 900° C. Some carbon dioxide was produced during the first 2 minutes of the reaction period; however, over the entire reaction period, the average methane conversion was greater than 95% and the selectivity for hydrogen and carbon monoxide was greater than 80%. The average formation rates for hydrogen and carbon monoxide were respectively 526 µmol/min/g and 235 µmol/min/g. Carbon dioxide and higher hydrocarbons were produced in relatively small amounts.

This example illustrates that methane can be reacted with adsorbed oxygen on a perovskite adsorbent at an elevated temperature to produce hydrogen and carbon monoxide as principal reaction products.

Although the invention has been described with particular reference to specific equipment arrangements and to a specific experiment, these features are merely exemplary of the invention and variations are contemplated. For example, the process can be carried out in multiple vessel systems comprising three or more vessels operated, for example, out of phase. Additionally, as noted above, the direction of hydrocarbon flow through the reaction vessels can be countercurrent to the direction of flow of air through the vessels. For instance, in the system illustrated in the appended drawing, hydrocarbon gas can be introduced into the system through line 48, flow downwardly through vessels A and B, and exit the system through line 14. As another alternative to the above-described process, the invention can be practiced by conducting the hydrocarbon partial oxidation step in the liquid phase. The scope of the invention is limited only by the breadth of the appended claims.

What is claimed is:

1. A process for producing hydrogen and carbon monoxide by the partial oxidation of at least one hydrocarbon comprising the steps:

(a) passing an oxygen-containing gas at a temperature in the range of about 300 to about 1400° C. through a reaction zone containing an oxygen-selective mixed conductor at an absolute pressure in the range of about 0.5 to about 50 bara, thereby preferentially adsorbing oxygen from said oxygen-containing gas onto said mixed conductor; and (b) passing said at least one hydrocarbon through said reaction zone at a temperature in the range of about 300 to about 1400° C., thereby contacting said mixed conductor and reacting with said oxygen adsorbed onto said mixed conductor to produce a product gas comprising hydrogen, carbon monoxide or mixtures of these.

2. The process of claim 1, wherein said oxygen-selective mixed conductor is selected from the group consisting of: (1) perovskite substances having the structural formula $A_{1-x}M_xBO_{3-\delta}$, where A is a rare earth ion, M is Sr, Ca, Ba or mixtures of these, B is Co, Mn, Cr, Fe or mixtures of these, x varies from 0 to 1 and δ is the deviation from stoichiometric composition resulting from the substitution of Sr, Ca and Ba for rare earth ions; (2) ceramic substances selected from the group consisting of $Bi_2O_3$, $ZrO_2$, $CeO_2$, $ThO_2$, $HfO_2$ and mixtures of these, the ceramic substance being doped with CaO, rare earth metal oxides or mixtures of these; (3) brownmillerite oxide; and (4) mixtures of any of these.

3. The process of claim 2, wherein said oxygen-selective mixed conductor is a ceramic substance of (2), said ceramic substance being doped with a rare earth metal oxide selected from the group consisting of $Y_2O_3$, $Nb_2O_3$, $Sm_2O_3$, $Gd_2O_3$ and mixtures of these.

4. The process of claim 1, wherein said oxygen-selective mixed conductor is a perovskite substance.

5. The process of claim 4, wherein x varies from about 0.1 to 1.

6. The process of claim 5, wherein A is La, Y or mixtures of these, M is Sr, Ca or mixtures of these and B is Co, Fe or mixtures of these.

7. The process of claim 6, wherein x is 0.2 to 1.

8. The process of claim 4, wherein A is La, Y or mixtures of these.

9. The process of claim 4, wherein M is Sr, Ca or mixtures of these.

10. The process of claim 4, wherein B is Co, Fe or mixtures of these.

11. The process of claim 1, claim 2 or claim 4, wherein said oxygen-containing gas is air.

12. The process of claim 11, further comprising, between steps (a) and (b), the additional step comprising: (1) purging said reaction zone with gas that is compatible with said product gas, (2) depressurizing said reaction zone, or (3) both purging said reaction zone with gas that is compatible with said product gas and depressurizing said reaction zone.

13. The process of claim 12, wherein the purge gas is oxygen, steam, carbon dioxide or mixtures of these.

14. The process of claim 11, further comprising, after step (b), removing said product gas from said reaction zone by: (1) purging said reaction zone with steam, carbon dioxide, nitrogen, argon, helium or mixtures of these, (2) depressurizing said reaction zone, or (3) both purging said reaction zone with steam, carbon dioxide, nitrogen, argon, helium or mixtures of these and depressurizing said reaction zone.

15. The process of claim 11, wherein said at least one hydrocarbon has an aliphatic, cycloaliphatic or aromatic structure and it contains 1 to 12 carbon atoms.

16. The process of claim 15, carried out at a temperature in the range of about 600 to about 1200° C.

17. The process of claim 16, wherein step (a) is carried out at an absolute pressure in the range of about 0.5 to 20 bara.

18. The process of claim 17, wherein said at least one hydrocarbon contains 1 to 6 carbon atoms.

19. The process of claim 18, carried out at a temperature in the range of about 750 to about 1100° C.

20. The process of claim 19, wherein said at least one hydrocarbon comprises methane.

21. The process of claim 20, wherein said at least one hydrocarbon comprises natural gas.

22. The process of claim 19, wherein said at least one hydrocarbon comprises a petroleum derivative.

23. The process of claim 22, wherein said petroleum derivative comprises naphtha, gasoline or mixtures thereof.

24. The process of claim 11, wherein said reaction zone additionally contains a catalyst selective for partial oxidation reactions.

25. The process of claim 24, wherein said catalyst is deposited on said oxygen-selective mixed conductor.

26. The process of claim 11, further comprising, during step (b), passing a moderating agent selected from steam, carbon dioxide and mixtures thereof through said reaction zone.

27. The process of claim 26, wherein said moderating agent is steam.

28. The process of claim 11, further comprising repeatedly performing steps (a) and (b) in sequence in said reaction zone.

29. The process of claim 11, wherein said reaction zone contains particulate material having a thermal conductivity greater than that of said oxygen-selective mixed conductor.

30. The process of claim 29, wherein said particulate material is mixed with said oxygen-selective mixed conductor.

31. The process of claim 29, wherein said particulate material is placed upstream, downstream or both upstream and downstream of said oxygen-selective mixed conductor.

32. Apparatus for the partial oxidation of hydrocarbons comprising:

(a) a reaction zone containing an oxygen-selective mixed conductor;

(b) means for introducing oxygen-containing gas into said reaction zone;

(c) means for introducing hydrocarbon feed into said reaction zone; and (d) means for removing a product stream from said reaction zone.

33. The apparatus of claim 32, wherein said oxygen-selective mixed conductor is selected from the group consisting of: (1) perovskite substances having the structural formula $A_{1-x}M_xBO_{3-\delta}$, where A is a rare earth ion, M is Sr, Ca, Ba or mixtures of these, B is Co, Mn, Cr, Fe or mixtures of these, x varies from 0 to 1 and $\delta$ is the deviation from stoichiometric composition resulting from the substitution of Sr, Ca and Ba for rare earth ions; (2) ceramic substances selected from the group consisting of $Bi_2O_3$, $ZrO_2$, $CeO_2$, $ThO_2$, $HfO_2$ and mixtures of these, the ceramic substance being doped with CaO, rare earth metal oxides or mixtures of these; (3) brownmillerite oxide; and (4) mixtures of any of these.

34. The apparatus of claim 33, further comprising: (a) means for heating said oxygen-containing gas; (b) means for heating said reaction zone; or (c) means for heating said oxygen-containing gas and said reaction zone.

35. The apparatus of claim 34, wherein said oxygen-selective mixed conductor is a perovskite substance.

36. The apparatus of claim 35, wherein x varies from about 0.1 to 1.

37. The apparatus of claim 36, wherein A is La, Y or mixtures of these.

38. The apparatus of claim 36, wherein M is Sr, Ca or mixtures of these.

39. The apparatus of claim 36, wherein B is Co, Fe or mixtures of these.

40. The apparatus of claim 36, wherein A is La, Y or mixtures of these, M is Sr, Ca or mixtures of these and B is Co, Fe or mixtures of these.

41. The apparatus of claim 40, wherein x is 0.2 to 1.

42. The apparatus of claim 34, wherein said oxygen-selective mixed conductor is a ceramic substance of (2), said ceramic substance being doped with a rare earth metal oxide selected from the group consisting of $Y_2O_3$, $Nb_2O_3$, $Sm_2O_3$, $Gd_2O_3$ and mixtures of these.

43. The apparatus of claim 32, claim 33, or claim 34, wherein said oxygen-containing gas is air.

44. The apparatus of claim 43, wherein said hydrocarbon contains 1–12 carbon atoms.

45. The apparatus of claim 44, wherein said hydrocarbon is gaseous.

* * * * *